US00PP15200P3

(12) United States Plant Patent
Kabbes

(10) Patent No.: US PP15,200 P2
(45) Date of Patent: Oct. 5, 2004

(54) *ANTHEMIS TINCTORIA* PLANT NAMED 'CHARME'

(50) Latin Name: *Anthemis tinctoria*
Varietal Denomination: Charme

(75) Inventor: Brian Kabbes, Suameer (NL)

(73) Assignee: Inspiration Plant CV, Lisse (NL)

( * ) Notice: Subject to any disclaimer, the term of this patent is extended or adjusted under 35 U.S.C. 154(b) by 0 days.

(21) Appl. No.: 10/680,183

(22) Filed: Oct. 8, 2003

(65) Prior Publication Data

US 2004/0068776 P1 Apr. 8, 2004

Related U.S. Application Data

(63) Continuation of application No. 10/152,807, filed on May 23, 2002, now abandoned.

(51) Int. Cl.[7] ..... A10H 5/00

(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—Burns Doane , Swecker, Mathis LLP

(57) ABSTRACT

A new and distinct *Anthemis tinctoria* cultivar is provided that is the result of a controlled breeding program. The plant displays a distinctive dwarf growth habit. Attractive intense golden yellow blossoms are formed in abundance on a substantially continuous basis from June to October. The foliage contrasts well with the golden yellow blossom coloration. Non-viable seeds are formed. The new cultivar is well suited for growing as attractive ornamentation in pots or in the landscape.

6 Drawing Sheets

Botanical/commercial classification: *Anthemis tinctoria*/ *Anthemis.*
Varietal denomination: cv. 'Charme'.

SUMMARY OF THE INVENTION

The new cultivar of *Anthemis tinctoria* was created by artificial pollination wherein two parents crossed which previously had been studied in the hope that they would contribute the desired characteristics. Plants of this species sometimes are identified as Golden Marguerite. The breeding program that created the new cultivar took place during 1993 to 1998 at Suameer, The Netherlands, with the first cross being made during July 1993. The object of the breeding program was to create a distinctive dwarf-type *Anthemis* plant that displays a long flowering season combined with reduced fertility.

The female parent (i.e., the seed parent) was formed by the crossing of *Anthemis tinctoria,* ssp. *fussii* and *Anthemis tinctoria,* cv. 'KK94/2' (non-patented in the United States). The male parent (i.e., the pollen parent) was formed by the crossing of *Anthemis tinctoria*, cv. 'KK96/17' (non-patented in the United States and *Anthemis tinctoria* ssp. *australis* (non-patented in the United States). The seeds resulting from the cross were sown and small plants were obtained which were physically and biologically different from each other. Selective study resulted in the identification of a single plant of the new cultivar of the present invention.

It was found that the new *Anthemis* plant of the present invention displays:

(a) a distinctive dwarf growth habit (b) forms in abundance on a substantially continuous basis attractive intense golden yellow ligulate blossoms (c) forms non-viable seeds, and (d) is well suited for growing as attractive ornamentation in pots or in the landscape.

The new cultivar well meets the needs of the horticultural industry in view of its distinctive combination of characteristics. Previously know *Anthemis* plants form longer stems and are significantly taller overall plants. The dwarf stature of the new cultivar renders it to be particularly well suited for growing as a distinctive border or patio plant.

The new variety can be readily distinguished from its parental cultivars in view of its distinctive growth habit. More specifically, the new variety unlike the parental varieties displays a short dwarf growth habit with more branching. Also, the flowering time of the new cultivar is considerably longer than that of the parental cultivars and continues until frost.

The new cultivar was first asexually reproduced by the use of cuttings on Mar. 12, 1998 at Suameer, The Netherlands. It has been demonstrated that characteristics of the new cultivar are firmly fixed and are retained through successive generations of asexual propagation.

The new cultivar of the present invention has been named 'Charme'. 'Charme' has not been observed under all possible environmental conditions to date. Accordingly, it is possible that the phenotype may vary somewhat with variations in the environment, such as temperature, light, day length, etc.

BRIEF DESCRIPTION OF THE PHOTOGRAPHS

The accompanying photographs depict typical plants of the new cultivar at an age of approximately two years while growing at Suameer, The Netherlands. In FIGS. 3 through 8 coloration by reference to The R.H.S. Colour Chart of The Royal Horticultural Society, London, is included.

DETAILED DESCRIPTION

Figure 1:
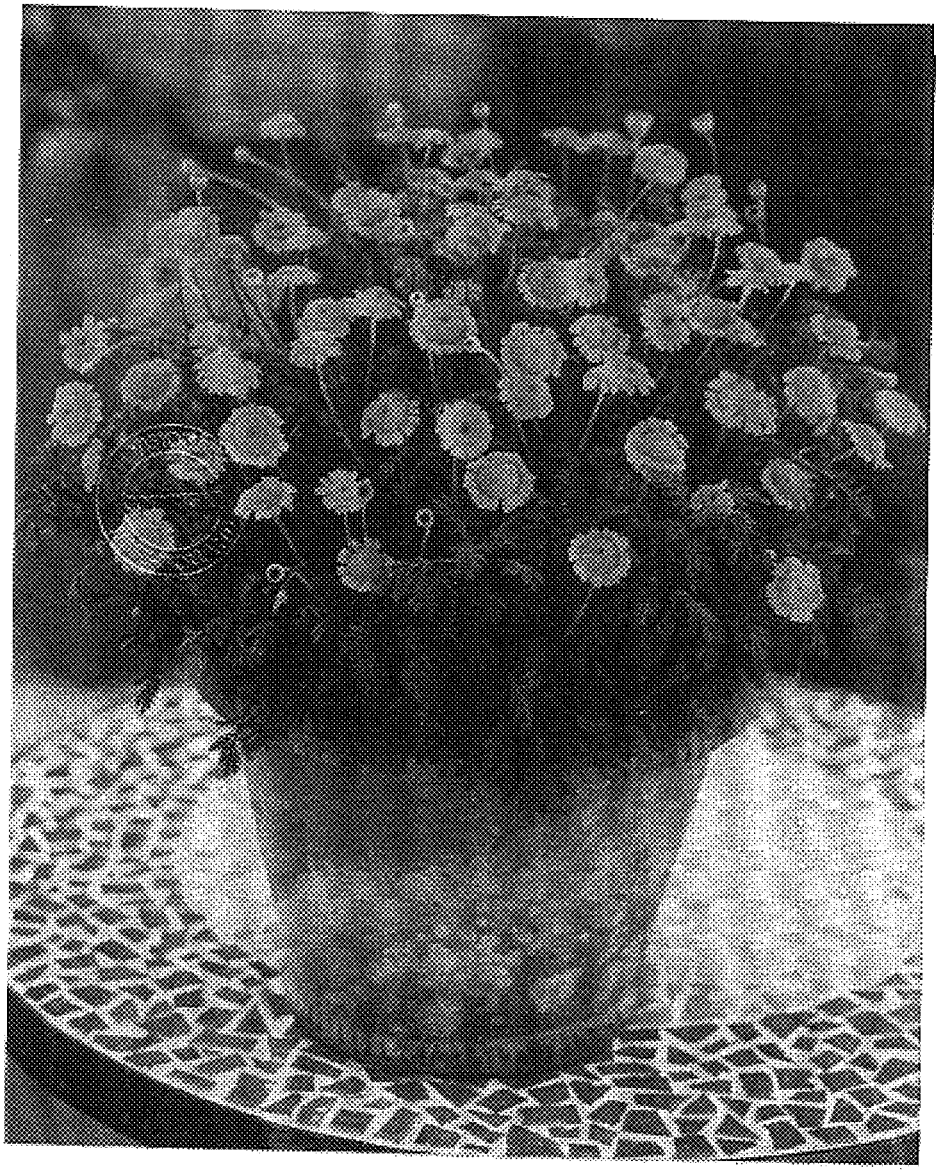
FIG. 1 shows a typical potted plant of the new 'Charme' cultivar wherein an abundance of intense golden yellow blossoms and green foliage are displayed.
Figure 2:
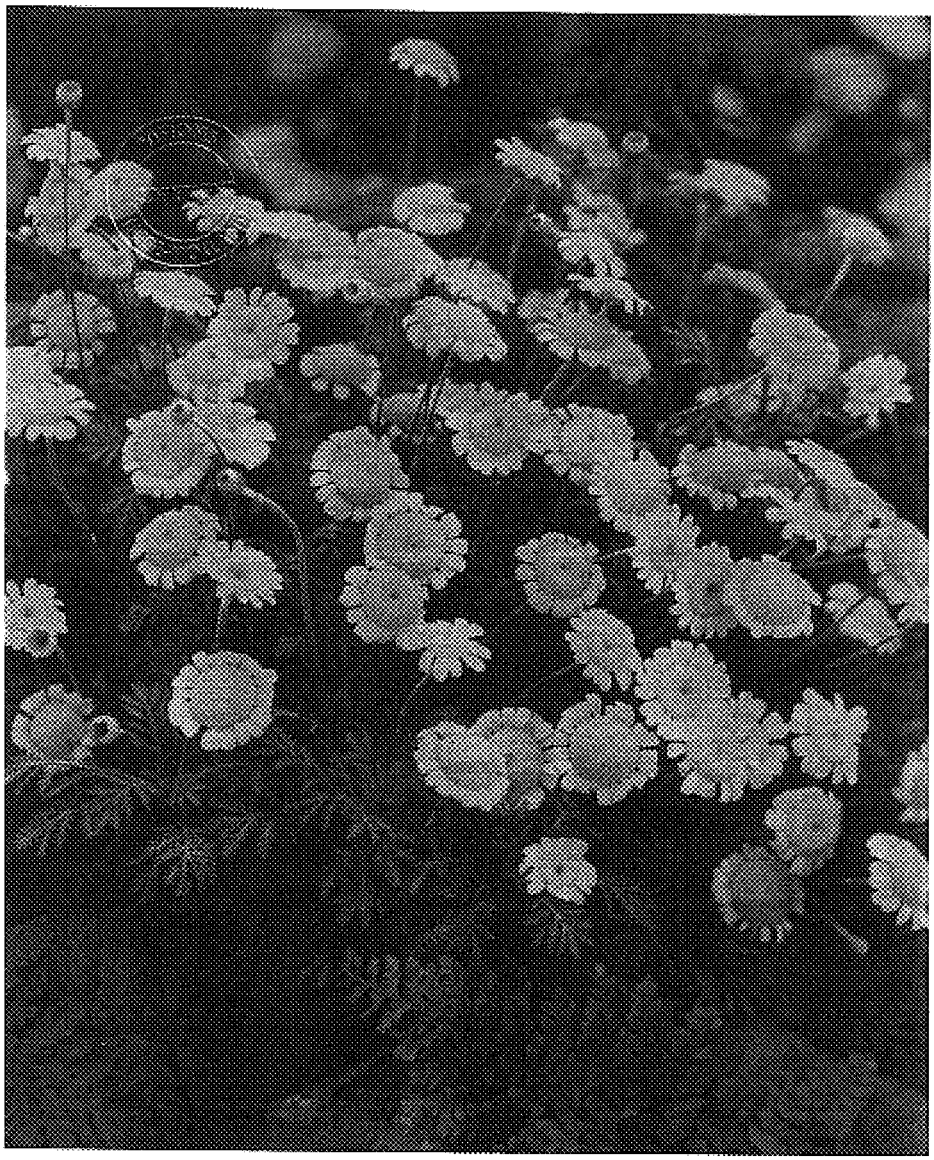
FIG. 2 shows a closer view of blossoms and green foliage.
Figure 3:
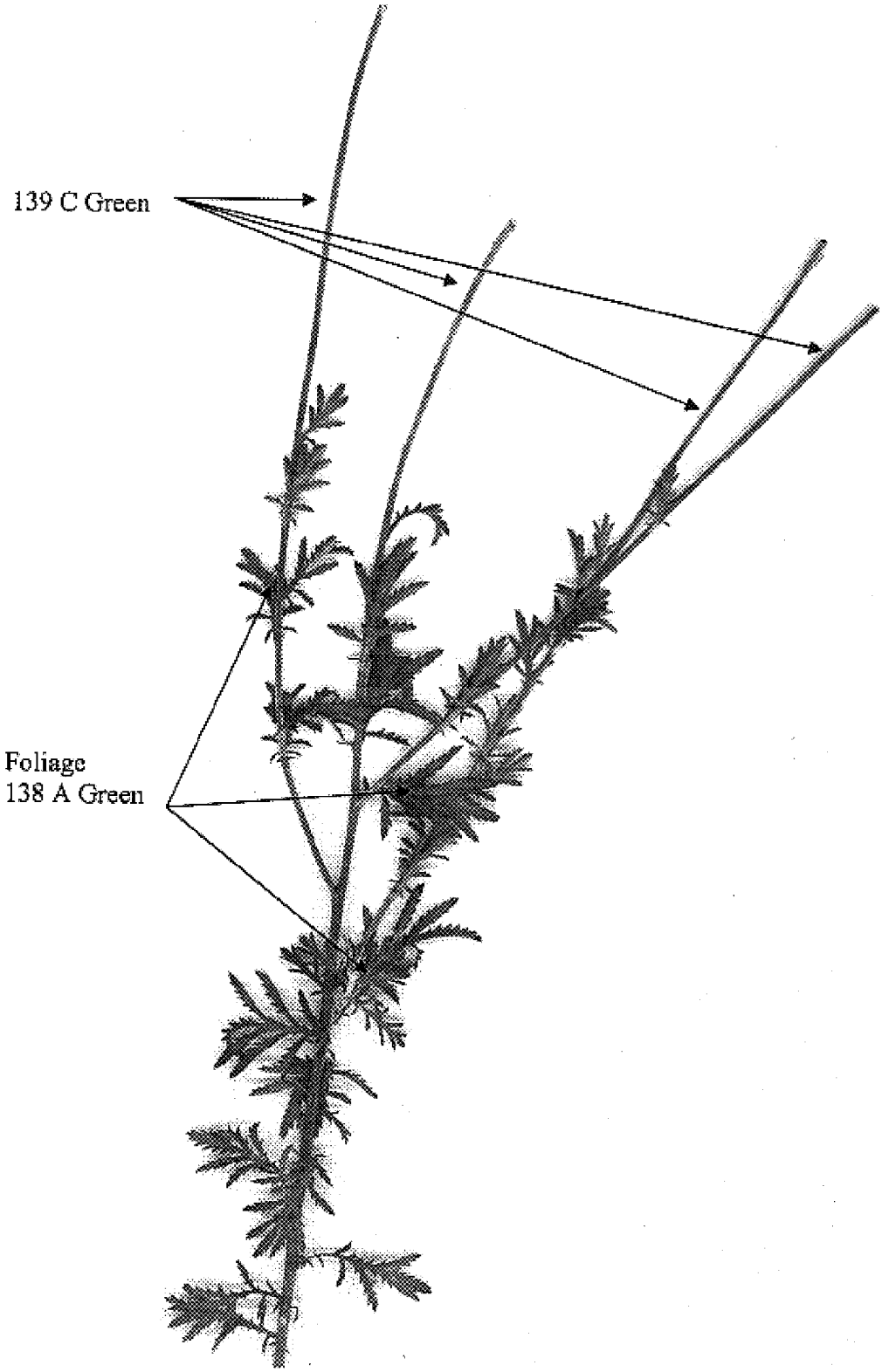
FIG. 3 shows a typical stems (flowers removed) with leaves.
Figure 4:
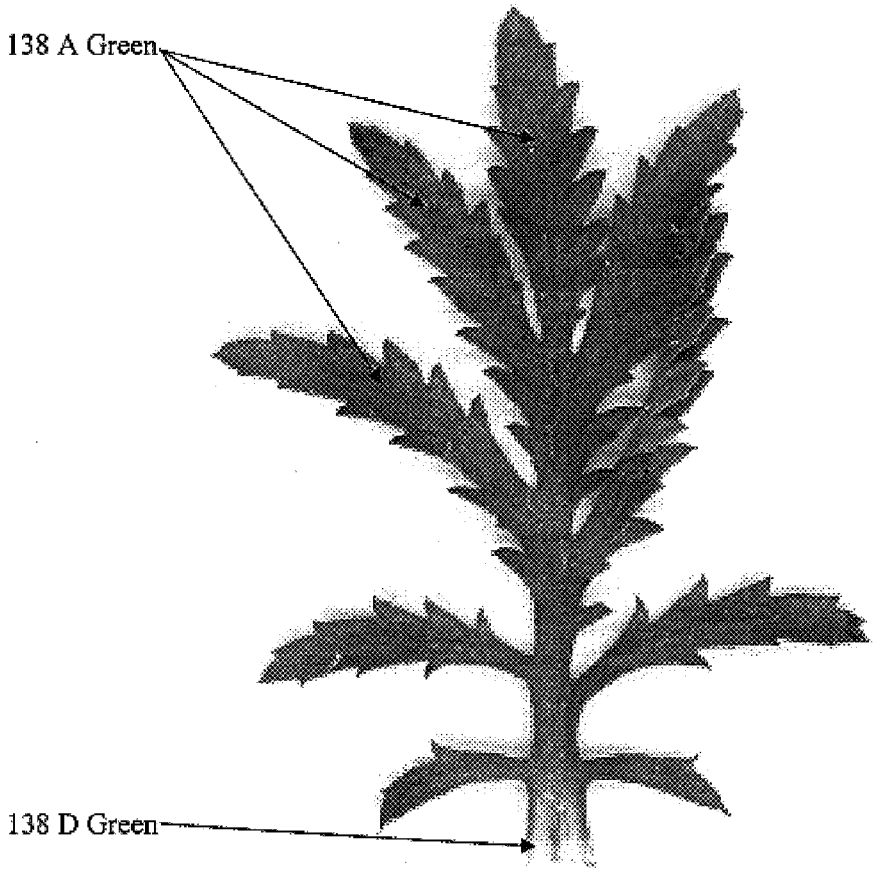
FIG. 4 shows a closer view of the upper surface of typical foliage.
Figure 5:
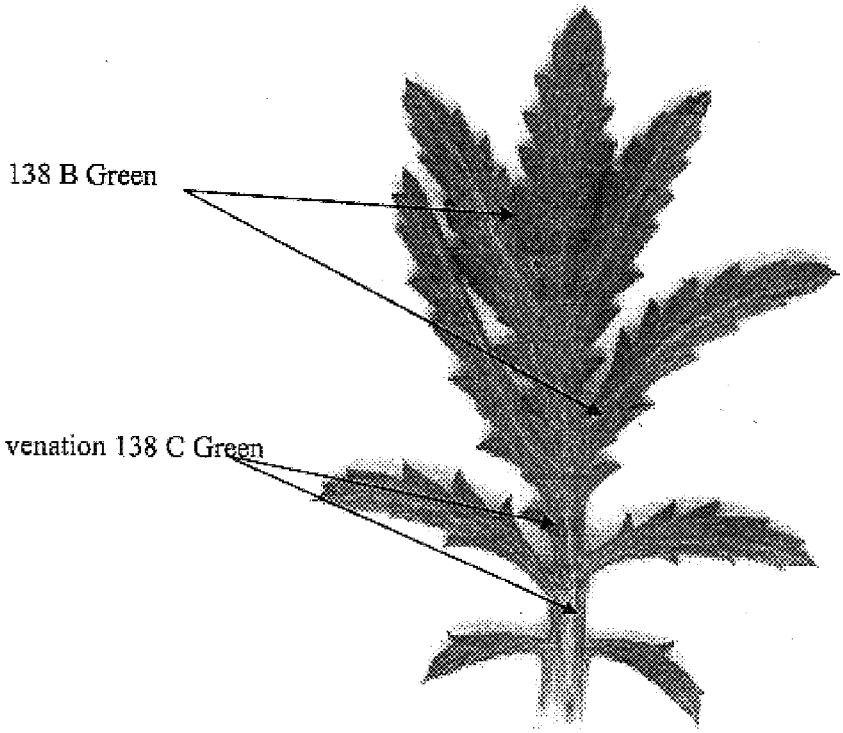
FIG. 5 shows a closer view of the under surface of typical foliage.
Figure 6:
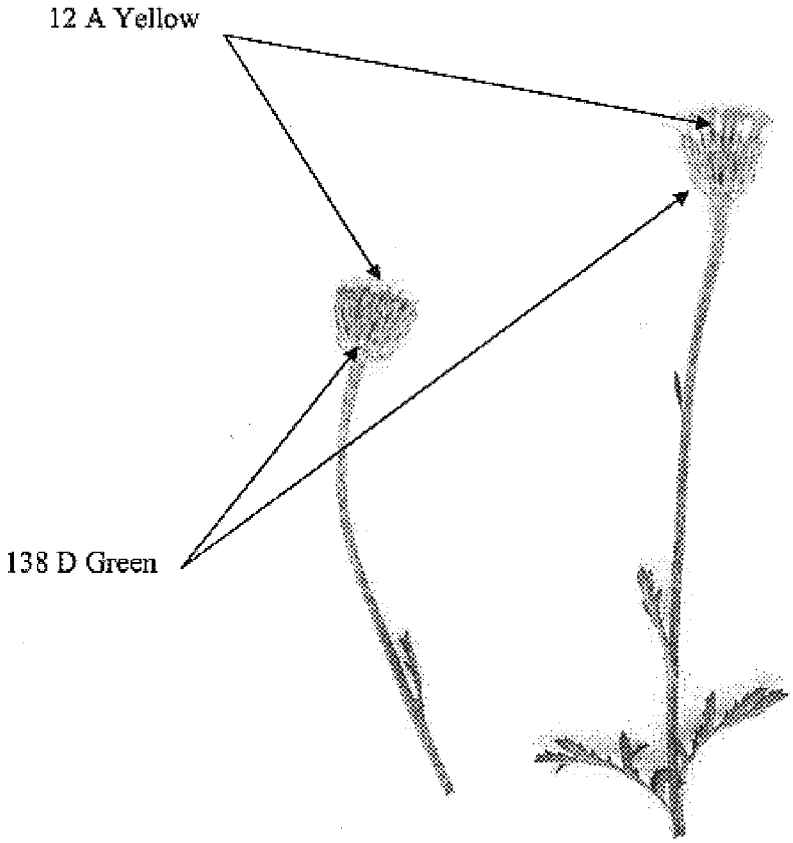
FIG. 6 shows typical floral buds when beginning to open while attached to stems and largely covered by ligules.
Figure 7:
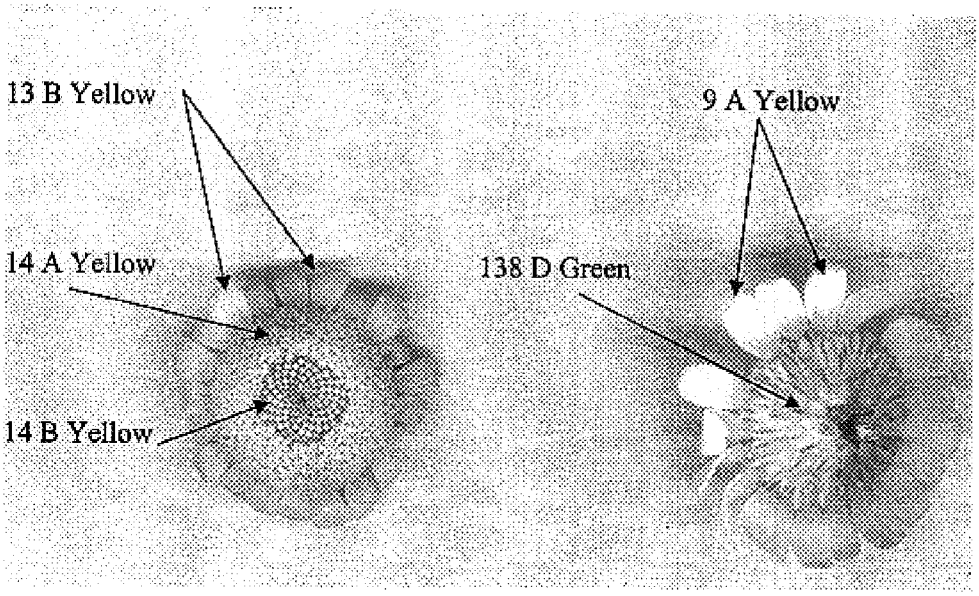
FIG. 7 shows a pair of opening flowers with the upper surface at the left and the lower surface at the right.
Figure 8:
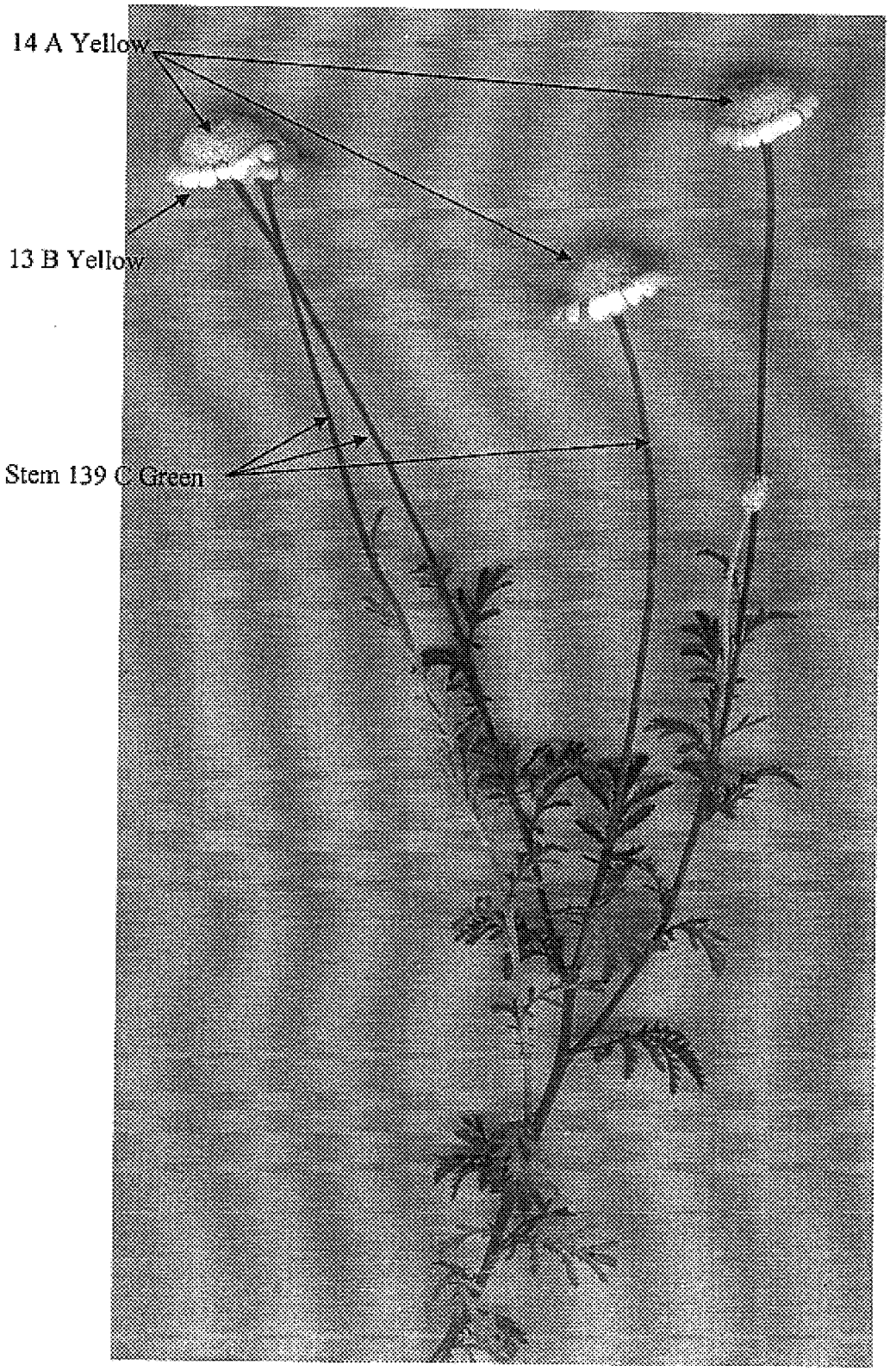
FIG. 8 shows typical stems with a cluster of opening flowers as well as a single bud in the course of opening.

The 'Charme' plants were reproduced from cuttings and were approximately two years in age and were grown pots at Suameer, The Netherlands. The color chart used in the identification of color is The R.H.S. Colour Chart of The Royal Horticultural Society, London.

Growth habit: Fast-growing dwarf perennial. A twelve week-old plant commonly displays a height of approximately 40 cm and a width of approximately 50 cm. As the plant further matures, there is an increasing width and little change in height. Previously known *Anthemis* plants commonly display a height at least approximately twice that of the new 'Charme' cultivar.

Foliage: Two-pinnasect with oblong to linear segments, and lanate on the under surface. The stems commonly are approximately 27 to 30 cm in length, approximately 2 mm in diameter, and possess a somewhat rough and hairy texture. The leaves tend to be randomly arranged along the stems, approximately 3 to 5 cm in length, approximately 1 to 2.5 cm in width, possess a cuspidate apex, possess a base that is asymmetrically attenuate, possess a serrate margin, possess a dull pubescent surface, are Green Group 138A in coloration on the upper surface when mature, are Green Group 138B in coloration on the under surface when mature, are slightly lighter green when immature, and possess a predominant central vein that is Green Group 138C. The foliage possesses a fragrance typical of *Anthemis* when crushed, and contrasts nicely with blossom coloration. The petiole commonly is approximately 4 mm in length, approximately 2 mm in diameter, and near Green Group 139 C in coloration.

Inflorescence: Forms in abundance attractive daisy-shaped ligulate blossoms. The floral buds are generally elliptical in configuration and are initially are largely covered by ligules. The mature floral buds commonly are approximately 10 to 15 mm in length and approximately 15 to 20 mm in diameter. At the bud stage the ray florets commonly are Yellow Group 12A in coloration. The ligules commonly are Green Group 138D in coloration. A fully open flower commonly is approximately 2.2 cm in diameter. The ray florets commonly number approximately 18 to 21 per flower, are generally elliptical in configuration, approximately 6 to 8 mm in length, approximately 2 to 2.5 mm in width, possess a rounded apex and a rounded base, and possess a smooth surface texture. The ray florets of a mature flower commonly are Yellow Group 13B in coloration on the upper surface and Yellow Group 9A in coloration on the under surface. The disc florets are extremely numerous (as illustrated), commonly are curved in configuration, approximately 0.2 cm in length, and possess a rounded apex and a triangular base. The disc florets commonly are Yellow Group 14A and 14B in coloration. The reproductive organs are present only among the disc florets, and their coloration commonly is indistinct and commonly generally varies from green to yellow. The filaments commonly are approximately 5 mm in length and the anthers commonly are approximately 0.5 mm in size. The styles commonly are approximately 3 mm in length and the stigma commonly is approximately 0.1 mm in size. The flowers are slightly fragrant. The peduncle commonly is approximately 10 to 15 cm in length, approximately 0.8 to 1.2 mm in diameter, bears a pubescent surface, and is Yellow-Green Group 139C in coloration. The flowering is substantially continuous from June to October with good reblooming. During 1999 the first flower appeared on June 11th, and last flower faded on October 18th.

Fertility: Some seeds are formed; however, no viable seeds have been observed during observations to date. Such seeds when formed are fluffy and brown in appearance, measure approximately 0.7 to 1.2 mm in size, and are non-fertile.

Disease/pest resistance: No special susceptibility to diseases and insects have been observed.

Drought/heat resistance: Good resistance to drought and heat has been displayed during observations to date.

Culture: Performs best in well-drained soil.

Hardiness: Can be grown in U.S.D.A. Hardiness Zone Nos. 3 to 9.

Usage: Provides attractive rich-flowering ornamentation when grown as a border plant or when potted and displayed on a patio.

I claim:

1. A new and distinct cultivar of *Anthemis tinctoria* plant is provided that displays:

(a) a distinctive dwarf growth habit, (b) forms in abundance on a substantially continuous basis attractive intense golden yellow ligulate blossoms, (c) forms non-viable seeds, and (d) is well suited for growing as attractive ornamentation in pots or in the landscape;

substantially as illustrated and described.

* * * * *